US00PP27955P2

(12) United States Plant Patent
Zaiger et al.

(10) Patent No.: US PP27,955 P2
(45) Date of Patent: May 2, 2017

(54) PEACH TREE NAMED 'SAUZEE GIANT'

(50) Latin Name: *Prunus persica*
Varietal Denomination: Sauzee Giant

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 43 days.

(21) Appl. No.: 14/756,817

(22) Filed: Oct. 19, 2015

(51) Int. Cl.
*A01H 5/08* (2006.01)

(52) U.S. Cl.
USPC ..... Plt./195

(58) Field of Classification Search
USPC ..... Plt./195
See application file for complete search history.

*Primary Examiner* — Keith Robinson

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Regular and productive bearer of large size fruit.
3. Fruit with good flavor and eating quality.
4. Mild, sweet, sub-acid, white flesh fruit.
5. Peento type fruit, with an attractive red blush.

1 Drawing Sheet

Botanical designation: *Prunus persica.*
Variety denomination: 'Sauzee Giant'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach trees, which are known to us, and mentioned herein, 'Sweet September' Peach (U.S. Plant Pat. No. 9,964) and the proprietary non-patented peach seedling selections '358LN87', '30LR286', '226LK547' and '375LN438'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. as a first generation cross between our proprietary non-patented peach seedling selections '358LN87' and '30LR286'. The seed parent (358LN87) originated as an open pollinated seedling selection from the proprietary non-patented peach '226LK547'. The pollen parent (30LR286) originated as an open pollinated seedling selection from the proprietary non-patented peach '375LN438'. A large number of these first generation seedlings were planted and grown on their own root system. Under close and careful observation we recognized the desirable tree and fruit characteristics of the present seedling and selected it in 2005 for additional asexual propagation and commercialization.

ASEXUAL REPRODUCTION OF THE VARIETY

In 2005 asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus persica*) is of large size, vigorous, upright growth and a regular and productive bearer of large size, white flesh, clingstone fruit with very good flavor and eating quality. The fruit is further characterized by its peento shape with good storage and shipping ability. In comparison to its proprietary non-patented peach seed parent (358LN87) the fruit of the new variety is peento shaped compared to globose and is approximately 21 days earlier in maturity. In comparison to its proprietary non-patented peach pollen parent (30LR286) the fruit of the new variety has white flesh compared to yellow and is approximately 24 days later in maturity. In comparison to the commercial variety 'Sweet September' Peach (U.S. Plant Pat. No. 9,964) the fruit of the new variety has white flesh compared to yellow, is clingstone compared to freestone and has a flat peento shape compared to globose.

DESCRIPTION OF THE PHOTOGRAPH

The accompanying color photographic illustration shows typical specimens of the foliage and fruit of the present new peach variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 10 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 10 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters in height and width the first growing season. Varies slightly with type and fertility of soil, climatic conditions and cultural practices.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 8 consecutive years. No alternate bearing observed.

*Fertility*.—Self fertile.

*Density*.—Medium dense, usually pruned to vase shape to increase air movement and sunlight to enhance fruit color and health of fruit wood.

*Hardiness*.—Hardy in all stone fruit growing areas of California. Tree grown in USDA Hardiness Zone 9. Winter chilling requirement approximately 850 hours at or below 45° F.

Trunk:

*Size*.—Large, average circumference 66.0 cm at 25.4 cm above ground on a 10 year old tree.

*Stocky*.—Medium stocky.

*Texture*.—Medium shaggy, roughness increases with age.

*Color*.—Varies from 10YR 4/2 to 2.5Y 4/2.

Branches:

*Size*.—Medium. Average circumference 18.0 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 27 in a 25.8 square cm section. Average length 5.3 mm. Average width 2.0 mm. Color varies from 7.5YR 7/6 to 7.5YR 6/6.

*Color*.—New growth varies from 5GY 5/8 to 7.5R 4/4 where exposed to the sun. Mature growth varies from 7.5YR 3/4 to 7.5YR 2/4, varies with age of growth.

Leaves:

*Size*.—Large. Average length 153.5 mm. Average width 43.8 mm.

*Form*.—Lanceolate.

*Apex*.—Acuminate.

*Base*.—Cuneate.

*Margin*.—Crenate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 11.5 mm. Average width 1.6 mm. Longitudinally grooved. Surface glabrous. Color varies from 5GY 5/6 to 5GY 4/8.

*Glands*.—Type — reniform. Size — medium. Average length 1.5 mm. Average diameter 0.7 mm. Number varies from 4 to 7, average number 5. Located primarily on base of leaf blade and upper portion of petiole. Color varies from 5GY 5/6 to 5GY 4/6.

*Stipules*.—Average number 2. Average length 12.3 mm. Edges — pectinate. Color varies from 2.5GY 4/6 to 5GY 4/8.

*Color*.—Upper surface varies from 5GY 3/6 to 5GY 3/4. Lower surface varies from 2.5GY 5/4 to 2.5GY 4/4. Midvein color varies from 10Y 8/2 to 7.5Y 8.5/2.

Flower buds:

*Size*.—Large. Average length 17.6 mm. Average diameter 9.2 mm.

*Hardiness*.—Hardy with respect to California winters.

*Density*.—Dense.

*Form*.—Conical, becoming elongated just before opening.

*Pedicel*.—Average length 4.4 mm. Average width 1.3 mm. Surface — glabrous. Color varies from 5GY 8/10 to 5GY 6/10.

*Color*.—Varies from 7.5RP 9/2 to 7.5RP 5/14.

Flowers:

*Blooming period*.—Date of First Bloom Feb. 28, 2015. Date of Petal Fall Mar. 10, 2015, varies slightly with climatic conditions.

*Size*.—Large, showy. Average height 20.1 mm. Average diameter 43.5 mm.

*Petals*.—Normally 5, alternately arranged to sepals. Size — large. Average length 22.7 mm. Average width 16.8 mm. Form — elliptical. Margin — sinuate. Arrangement — free. Petal apex — rounded. Petal base — truncate. Color varies from 7.5RP 9/2 to 7.5RP 5/14. Both upper and lower surfaces glabrous.

*Sepals*.—Normally 5, alternately arranged to petals. Size — large. Average length 8.5 mm. Average width 8.0 mm. Shape — ovate to triangular. Margin — entire. Apex — rounded to triangular. Surface — upper surface glabrous, lower surface pubescent. Color — upper surface varies from 5GY 5/10 to 5RP 3/10. Lower surface 5RP 3/10.

*Stamens*.—Average number per flower 49. Average filament length 17.0 mm. On average the stamens are above the height of the petals. Filament color varies from N 9.5/(white) to 5RP 7/10 depending on age of flower. Anther color varies from 7.5R 3/12 to 5Y 8/8.

*Pollen*.—Self fertile. Color varies from 2.5Y 7/12 to 5Y 7/12.

*Pistil*.—Number — normally one. Average length 11.7 mm. Surface — pubescent. Position of stigma an average of 7.5 mm below anthers. Color varies from 2.5GY 8/4 to 5GY 7/4.

*Fragrance*.—Wanting.

*Color*.—Varies from 7.5RP 9/2 to 7.5RP 5/14.

*Pedicel*.—Average length 4.5 mm. Average width 1.3 mm. Color varies from 5GY 7/6 to 5GY 7/12.

*Number flowers per flower bud*.—Normally one.

Fruit:

*Maturity when described*.—Firm ripe and ready for consumption.

*Date of first picking*.—Sep. 10, 2015.

*Date of last picking*.—Sep. 20, 2015, varies slightly with climatic conditions.

*Size*.—Large. Average diameter axially 47.0 mm. Average transversely in suture plane 83.7 mm. Average weight 247.1 grams, varies slightly with fertility of the soil, amount of thinning and climatic conditions.

*Form*.—Peento shape.

*Suture*.—Lipped.

*Ventral surface*.—Lipped.

*Apex*.—Retuse.

*Base*.—Retuse.

*Stem cavity*.—Rounded to slightly elongated in suture plane. Average depth 7.0 mm. Average diameter 14.2 mm.

Stem:

*Size*.—Medium. Average length 10.4 mm. Average diameter 3.9 mm.

*Color*.—Varies from 5GY 6/6 to 5GY 5/8.

Flesh:

*Ripens*.—Evenly.

*Texture*.—Firm, meaty.

*Fibers*.—Few, small, tender.

*Firmness*.—Good, comparable to other peach varieties.

*Aroma*.—Moderate.

*Amydgalin*.—Undetected.

*Eating quality*.—Very good.

*Flavor*.—Very good, sweet, mild, sub-acid.

*Juice*.—Moderate amount, enhances flavor.

*Acidity*.—Not available.

*Brix*.—Average Brix 14.0°, varies slightly with amount of fruit per tree and climatic conditions.

*Color*.—Varies from 2.5Y 9/2 to 10YR 9/2.

*Pit cavity*.—Average length 19.3 mm. Average width 12.2 mm. Average depth 27.0 mm. Color 5R 4/10 to 7.5YR 7/4.

Skin:

*Thickness*.—Medium.

*Surface*.—Smooth.

*Pubescence*.—Moderate, short in length.

*Tendency to crack*.—None.

*Color*.—Ground color varies from 7.5Y 9/2 to 7.5Y 8.5/2. Partially overspread with 7.5R 5/8 to 7.5R 6/8.

*Tenacity*.—Tenacious to the flesh.

*Astringency*.—Slight to none.

Stone:

*Type*.—Clingstone, strong adherence to flesh.

*Size*.—Medium. Average length 18.3 mm. Average width 26.0 mm. Average thickness 22.4 mm.

*Form*.—Globose.

*Base*.—Flat.

*Apex*.—Round.

*Surface*.—Pitted throughout, pits vary from rounded to elongated.

*Sides*.—Unequal, one side extending further from the suture plane.

*Ridges*.—Relatively smooth, extending from base to apex.

*Tendency to split*.—None.

*Color*.—Varies from 10R 3/6 to 7.5R 3/6 when dry.

Kernel:

*Size*.—Large. Average length 10.6 mm. Average width 11.0 mm. Average depth 8.6 mm.

*Form*.—Globose.

*Viability*.—Viable, complete embryo development.

*Skin color*.—Varies from 5Y 9/6 to 7.5Y 9/4.

Use: Dessert.

*Market*.—Local and long distance.

Keeping quality: Good, held firm in cold storage at 38° to 42° F. for 3 weeks without internal breakdown of flesh or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices. The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

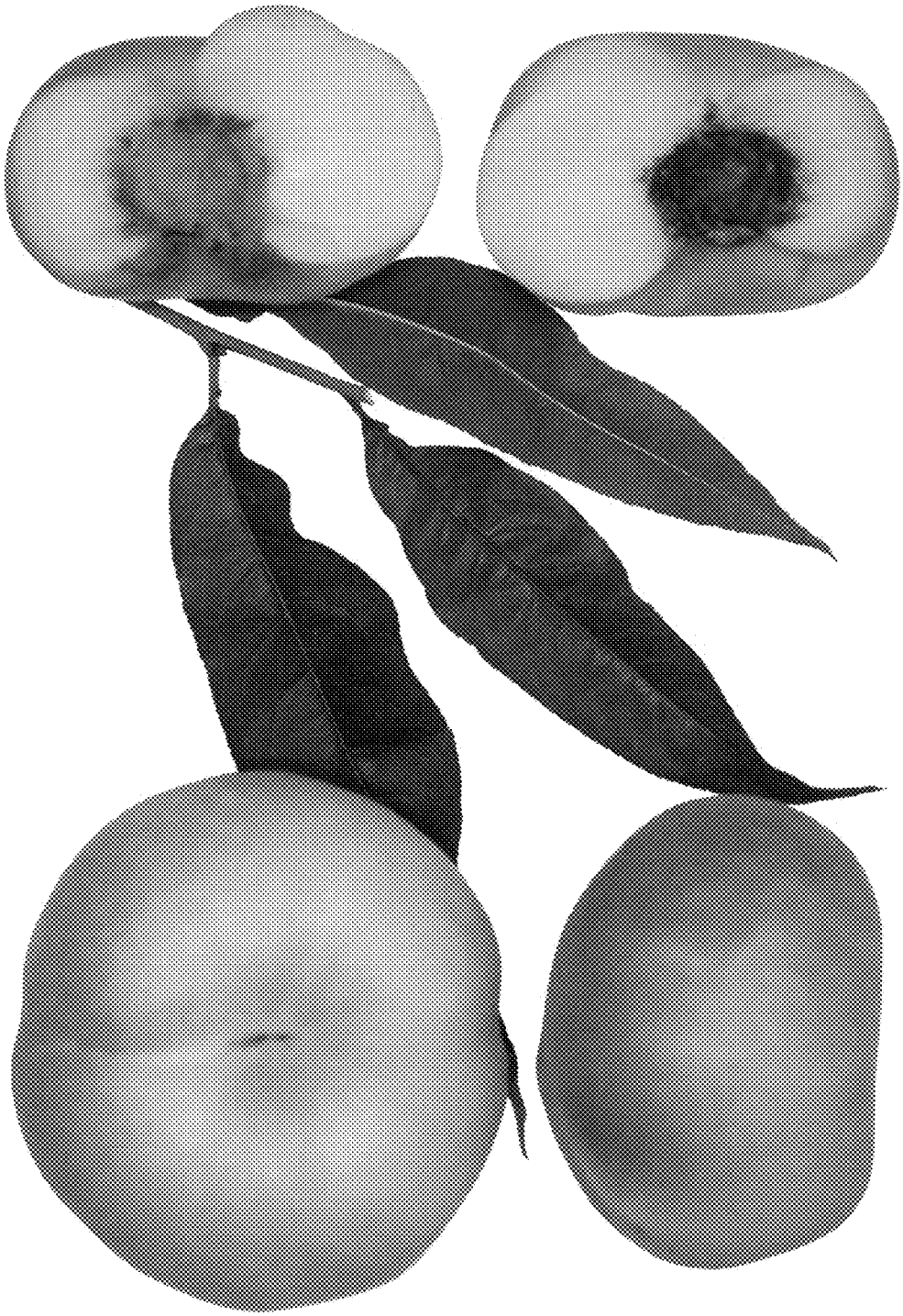

* * * * *